US012787999B2

(12) United States Patent
Drori

(10) Patent No.: US 12,787,999 B2
(45) Date of Patent: Nov. 10, 2026

(54) WEARABLE PASSIVE LICE ELIMINATOR

(71) Applicant: Noam Drori, Yavne (IL)

(72) Inventor: Noam Drori, Yavne (IL)

( * ) Notice: Subject to any disclaimer, the term of this patent is extended or adjusted under 35 U.S.C. 154(b) by 180 days.

(21) Appl. No.: 18/536,294

(22) Filed: Dec. 12, 2023

(65) Prior Publication Data

US 2024/0215564 A1 Jul. 4, 2024

Related U.S. Application Data

(60) Provisional application No. 63/436,882, filed on Jan. 4, 2023.

(51) Int. Cl.

| | |
|---|---|
| ***A01M 1/22*** | (2006.01) |
| ***A01M 1/02*** | (2006.01) |
| ***A01M 1/04*** | (2006.01) |
| ***A01M 29/10*** | (2011.01) |
| ***A01M 29/12*** | (2011.01) |
| ***A61B 17/50*** | (2006.01) |
| ***A61N 5/06*** | (2006.01) |
| *A61B 17/00* | (2006.01) |

(52) U.S. Cl.

CPC ............ *A01M 1/223* (2013.01); *A01M 1/023* (2013.01); *A01M 1/04* (2013.01); *A01M 29/10* (2013.01); *A01M 29/12* (2013.01); *A61B 17/50* (2013.01); *A61N 5/0616* (2013.01); *A61B 2017/00747* (2013.01); *A61B 2017/505* (2013.01)

(58) Field of Classification Search

CPC .......... A01M 1/02; A01M 1/00; A01M 1/023; A01M 1/04; A01M 1/223; A61B 2017/505

See application file for complete search history.

(56) References Cited

U.S. PATENT DOCUMENTS 1,780,408 A * 11/1930 Smith .................. A01M 29/12 2/171.2
2,307,163 A * 1/1943 Shea ...................... A01M 1/02 43/112
5,155,950 A * 10/1992 Burgeson ............. A41D 13/001 119/857
5,178,168 A * 1/1993 Kantor ................... A45B 24/00 132/219
5,775,261 A * 7/1998 Shaw .................... A01M 1/223 119/482
6,584,349 B1 * 6/2003 Sage, Jr ............... A61N 1/0444 604/20
6,708,050 B2 * 3/2004 Carim .................. A61B 5/0006 604/20
6,936,269 B2 * 8/2005 Robinson ...................... 424/409
7,661,151 B2 2/2010 Pienaar
9,307,820 B2 4/2016 Ritterband et al.
2002/0099320 A1 * 7/2002 Beck .................... A61N 1/0492 604/20
2004/0267237 A1 * 12/2004 Sun ........................ A61N 1/044 604/501

(Continued)

FOREIGN PATENT DOCUMENTS

AU 2023421577 A1 8/2025
CN 106259243 A * 1/2017 ............ A01M 1/223

(Continued)

*Primary Examiner* — Carly W. Lynch

(57) ABSTRACT

A system and method for treating head lice, and, more particularly, but not exclusively, to a system to trap and/or eradicate head lice from a subject passively.

18 Claims, 9 Drawing Sheets

(56) References Cited

U.S. PATENT DOCUMENTS

Figure 1:
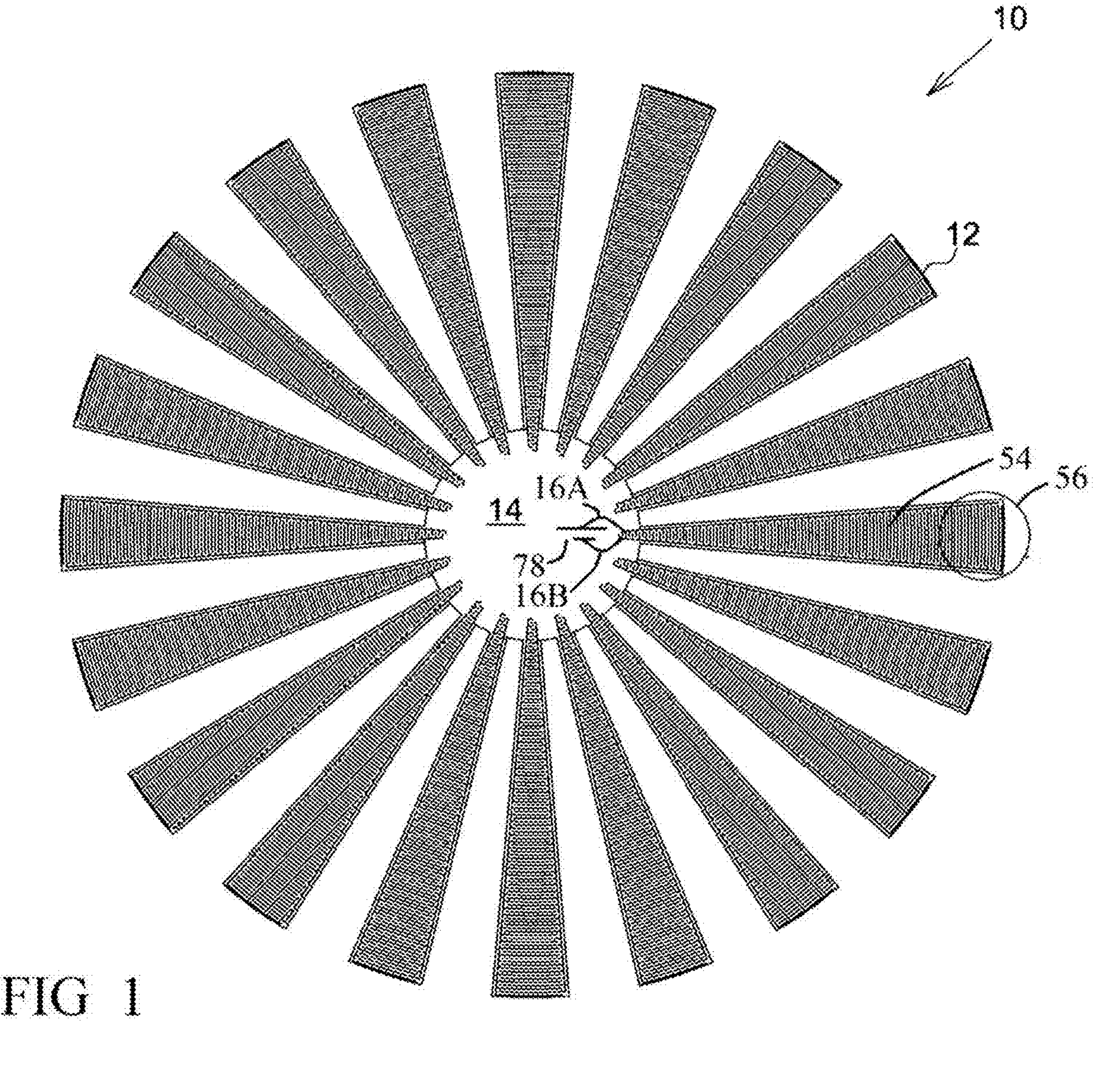

| | | | | |
|---|---|---|---|---|
| 2006/0260183 | A1 * | 11/2006 | Hockaday | A01M 1/02 43/132.1 |
| 2006/0280765 | A1 * | 12/2006 | Kuenen | C07C 11/21 514/762 |
| 2010/0049286 | A1 * | 2/2010 | Thorsen | A61F 7/00 607/107 |
| 2010/0057147 | A1 * | 3/2010 | Fassih | A61K 9/0009 607/2 |
| 2010/0145417 | A1 * | 6/2010 | Kaufmann | A01M 1/2094 607/91 |
| 2010/0158965 | A1 * | 6/2010 | Beitzel | A01N 25/34 424/405 |
| 2013/0133587 | A1 * | 5/2013 | Pelfrey | A01K 13/00 119/625 |
| 2014/0328790 | A1 * | 11/2014 | Saguchi | A01N 37/06 424/84 |
| 2015/0128877 | A1 * | 5/2015 | McIntyre | A01M 29/12 119/712 |
| 2017/0028184 | A1 * | 2/2017 | Godden | A61N 1/0416 |
| 2019/0066475 | A1 * | 2/2019 | Bordelon | A01M 29/24 |
| 2022/0095606 | A1 * | 3/2022 | Campbell | A45D 8/36 |

FOREIGN PATENT DOCUMENTS

| | | | | | |
|---|---|---|---|---|---|
| CN | 110115263 | A | * | 8/2019 | A01M 29/28 |
| CN | 220712621 | U | * | 4/2024 | A01M 3/00 |
| CN | 118285358 | A | | 7/2024 | |
| DE | 102009045498 | A1 | * | 4/2011 | A45D 24/00 |
| EP | 1009201 | A2 | * | 6/2000 | H01B 1/22 |
| EP | 4646103 | A1 | | 11/2025 | |
| HK | 40109429 | A | | 12/2024 | |
| IL | 309316 | A | | 8/2024 | |
| WO | WO-2012/160023 | A1 | * | 11/2012 | A45D 24/30 |
| WO | WO-2018109417 | A1 | * | 6/2018 | A01M 1/103 |
| WO | 2024147128 | A1 | | 7/2024 | |
| ZA | 202400025 | B | | 9/2024 | |

* cited by examiner

WEARABLE PASSIVE LICE ELIMINATOR

RELATED APPLICATION/S

This application claims the benefit of priority under 35 USC § 119(e) of U.S. Provisional Patent Application No. 63/436,882 filed 4 Jan. 2023, the contents of which are incorporated herein by reference in their entirety.

TECHNICAL FIELD

The present invention, in some embodiments thereof, relates to a system and method for treating head lice, and, more particularly, but not exclusively, to a system to trap and/or eradicate head lice from a subject passively.

BACKGROUND OF THE INVENTION

Head lice are small, wingless insects that live on the human scalp and feed on blood. Head lice prefer to live in warm, moist environments, such as the scalp, which provides them with a source of food and shelter. Lice attach themselves to the hair shafts and feed on the dead skin cells and oils that build up on the scalp.

Head lice are attracted to the heat generated by the human body, smell of sweat which contains amino acids and other proteins that lice feed on, the carbon dioxide that humans exhale, and are also attracted to the vibrations that humans create when they move. In addition to these physical factors, lice are also attracted to the pheromones of other lice, results in lice colonies.

Head lice are contagious and can spread easily from person to person through close head-to-head contact or through contact with infested objects, such as hats, combs, brushes towels and bedding.

The bites of head lice can cause the scalp to itch and feel uncomfortable. Additionally, scratching can lead to sores and infection. Further, untreated head lice may degrade the scalp and affect its health. Head lice are often associated with poor hygiene, which can lead to social isolation and bullying, causing social stigma. However, head lice are attracted to hair that is clean and free of oil, as this provides a better grip on the hair shaft.

Head lice can be difficult to get rid of Head lice eggs, called nits, are difficult to remove from the hair. Over-the-counter treatments are not always effective, and prescription treatments can be expensive. Often, conventional treatment needs to be repeated over several days or weeks. Eradicating the nits and adolescent head lice is vital and often requires combing of the hair with a fine-toothed comb after and/or during treatment. Effective combing may be difficult to achieve in long hair, curly hair, dense hair, especially in young children who refuse sit still for long periods of time and are sensitive to the painful hair pulling of a tight comb.

Therefore, there is a long felt need to provide an efficient solution to eradicating head lice.

SUMMARY OF THE INVENTION

According to an aspect of some embodiments of the invention, there is provided a device for eliminating a pest on a host, including: an eliminator configured to neutralize the pest an attachment mechanism for holding the eliminator in a position where movement of the pest will bring it to be neutralized by the eliminator.

According to some embodiments of the invention, the eliminator includes opposite electric poles configured to shock the pest.

According to some embodiments of the invention, the electrical eliminator includes one or more electrifying sheets.

According to some embodiments of the invention, the oner or more electrify sheets connect at a focal point.

According to some embodiments of the invention, the device further includes shielding.

According to some embodiments of the invention, the device further includes an insulating sheet.

According to some embodiments of the invention, the eliminator includes a trap, adhesive, a poison, or any combination thereof.

According to some embodiments of the invention, the device further includes stimulator configured to stimulate movement of the pest.

According to some embodiments of the invention, means of stimulating movement of the pest is chemical and/or physical.

According to some embodiments of the invention, the physical stimulator is a light source or vibration source.

According to some embodiments of the invention, the stimulator is configured to repel the pest.

According to some embodiments of the invention, the stimulator is configured to attract the pest.

According to some embodiments of the invention, the chemical stimulator is selected from the group consisting of pheromones, Soursop, coconut, tea tree oil, lavender oil, *Eucalyptus* oil, rosemary oil, lemon grass oil, vinegar, neem, garlic, masha, peppermint oil, and any combination thereof.

According to some embodiments of the invention, the device further includes a compartment located at a focal point of the device and configured for storing the chemical stimulator.

According to some embodiments of the invention, the compartment includes a pin configured to puncture a replaceable capsule containing a chemical stimulator or poison.

According to some embodiments of the invention, the compartment includes a plurality of wicks extending through openings in the compartment for distributing the stimulator.

According to some embodiments of the invention, the absorbent strips are configured for distribution of the chemical stimulator or poison.

According to some embodiments of the invention, the device is configured to be worn as an item of clothing, attached to bedding, worn under clothing, placed near the body and/or in contact with the body of the subject.

According to some embodiments of the invention, the device is worn over the head of human host.

According to some embodiments of the invention, the attachment mechanism is one or more straps, adhesive, fitted to the body, built into an item of clothing and/or attached to an item of clothing.

According to an aspect of some embodiments of the invention, there is provided a method for passively eliminating pests, the method including: positioning a pest eliminator near an infected host; interacting of the pest with the eliminator resulting from the pest's own movement; and neutralizing the pest as a result of the interacting.

According to some embodiments of the invention, the interacting includes contact of the pest with opposite charged electrodes.

According to some embodiments of the invention, the eliminating is by electrocuting, poisoning, trapping, or any combination thereof.

According to some embodiments of the invention, the electrocuting is by contacting the pest to electrodes of opposite polarity by their own movement.

According to some embodiments of the invention, the method further includes stimulating the movement of the pest.

According to some embodiments of the invention, the stimulating movement is by a chemical repellant.

According to some embodiments of the invention, stimulating is by supplying light or vibration.

According to some embodiments of the invention, the chemical stimulator is configured to repel the pest.

According to some embodiments of the invention, the chemical stimulating includes attracting the pest.

BRIEF DESCRIPTION OF THE SEVERAL VIEWS OF DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. The drawings are not necessarily drawn to scale.

In the figures:

FIG. 1: A schematic illustration of a lice killer device in a deployed state, in accordance with some embodiments.

Figure 2:
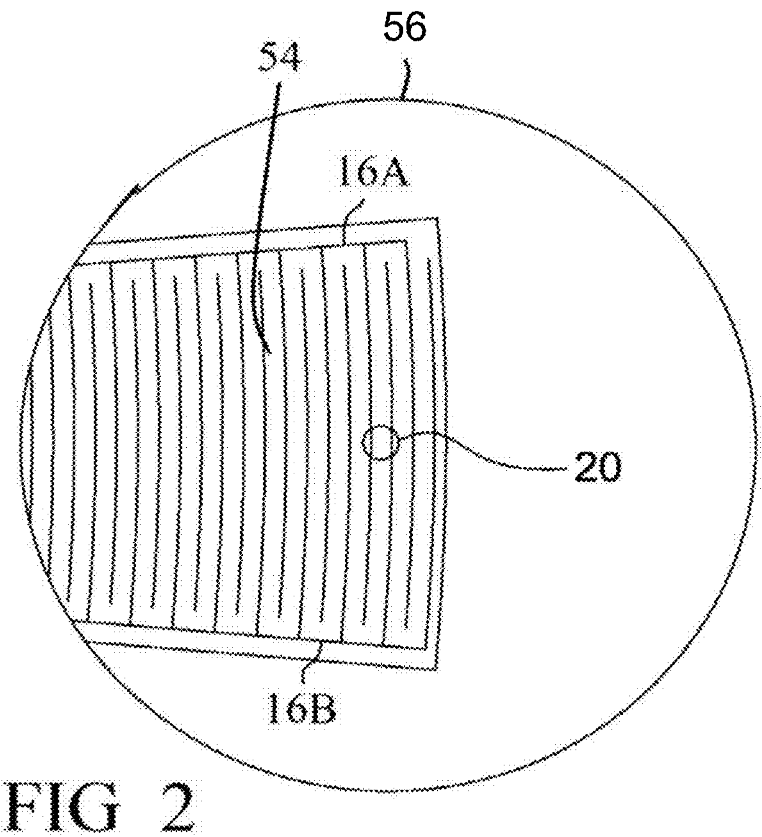

FIG. 2: An enlarged section of an end of one of the extension portions of the lice killer device of FIG. 1, in accordance with some embodiments.

Figure 3:
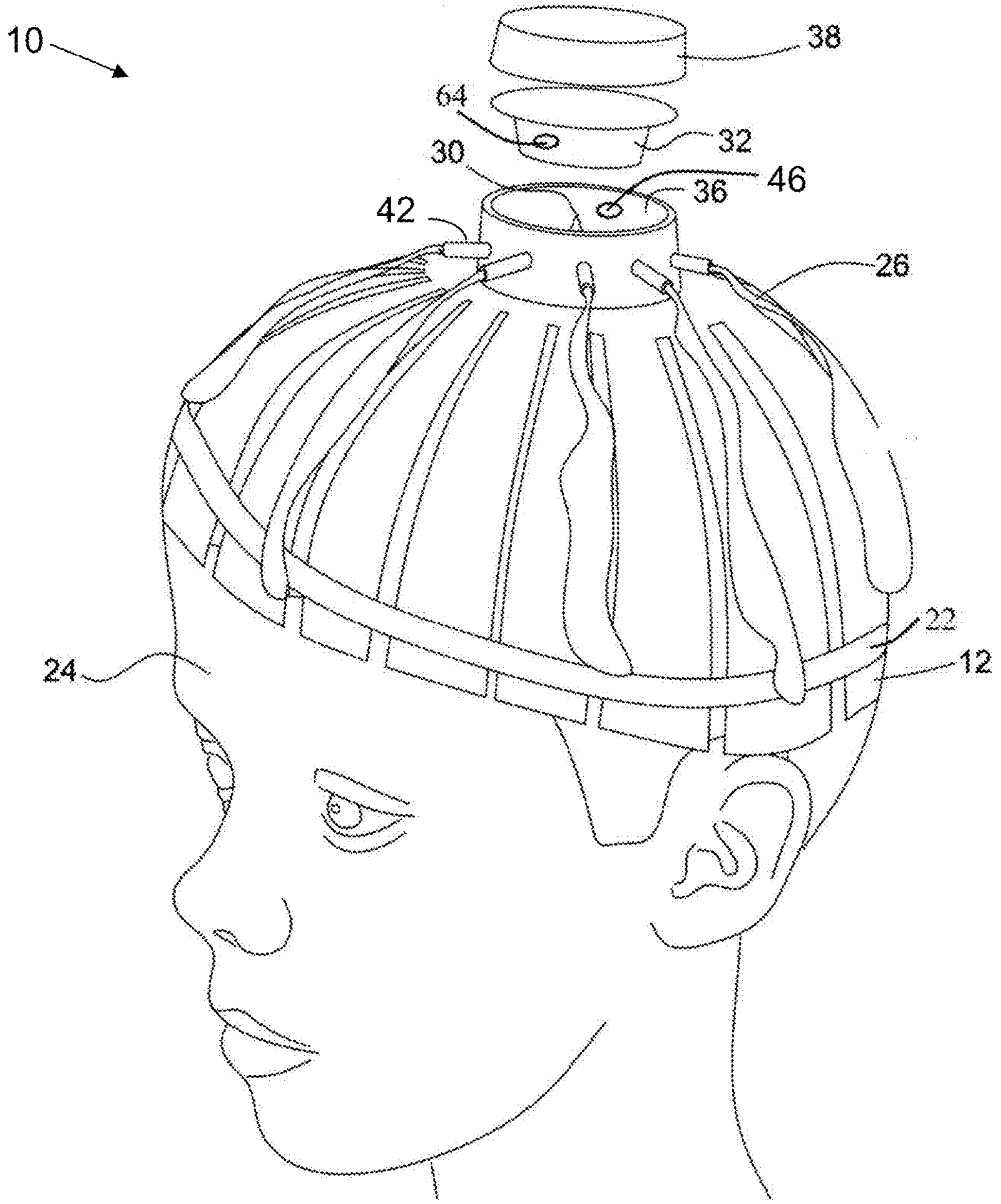

FIG. 3: A schematic illustration of a lice killer device positioned on a subject's head, in accordance with some embodiments.

Figure 4:
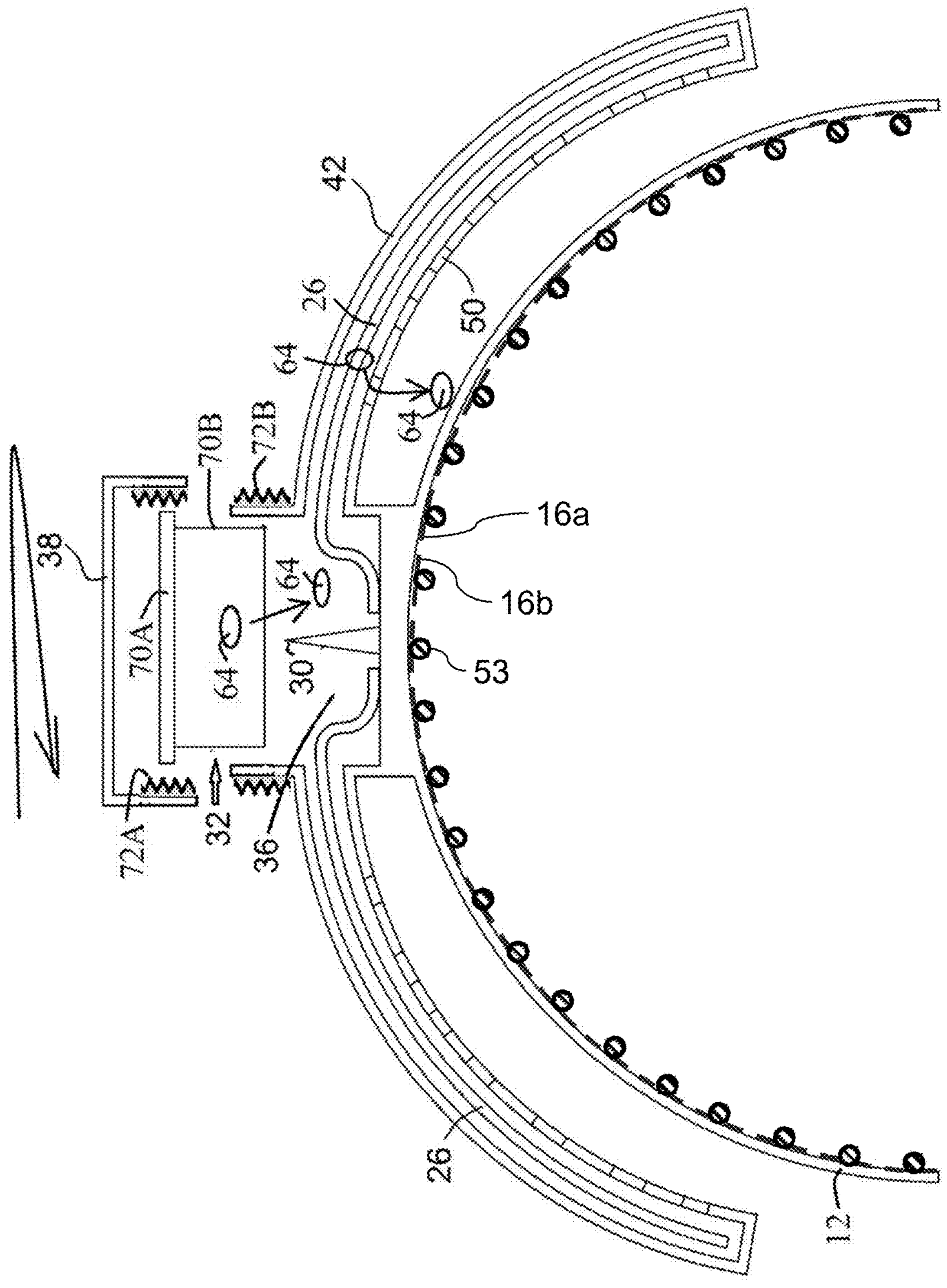

FIG. 4: A schematic illustration of a front sectional view of a lice killer device, in accordance with some embodiments.

Figure 5:
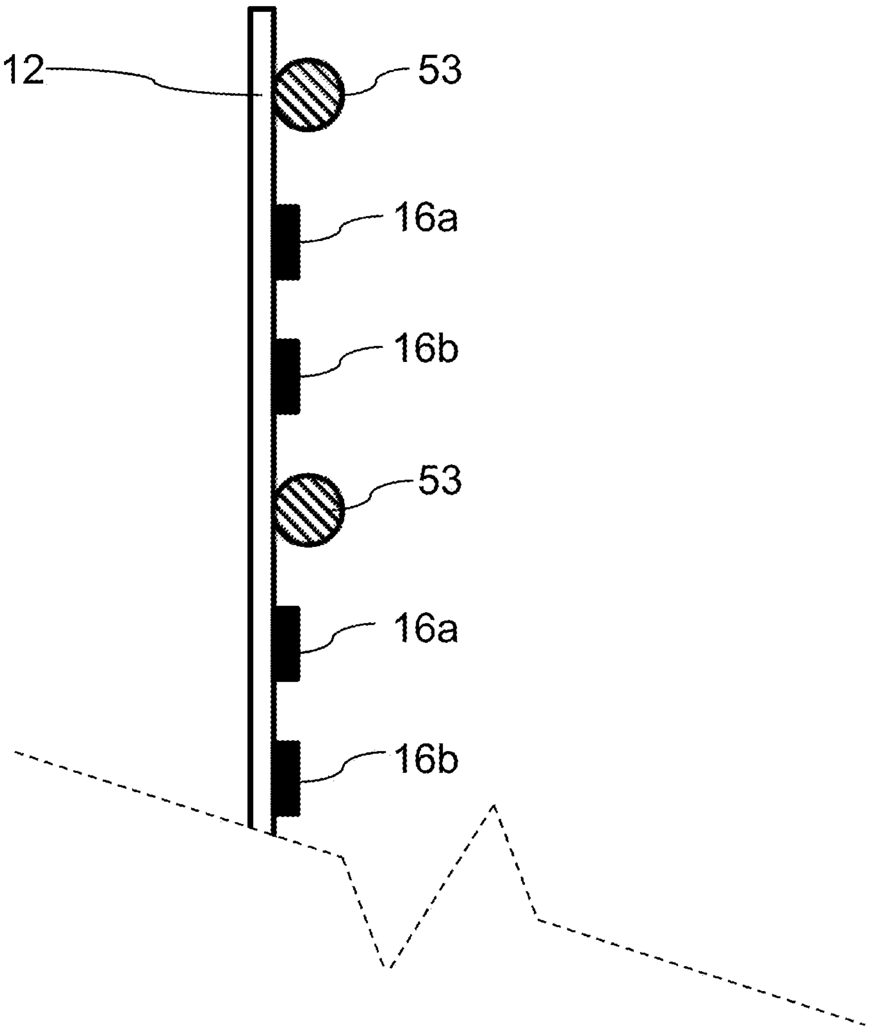

FIG. 5: A schematic illustration of a longitudinal cross section of electrifying sheet of a lice killer device, in accordance with some embodiments.

Figure 6:
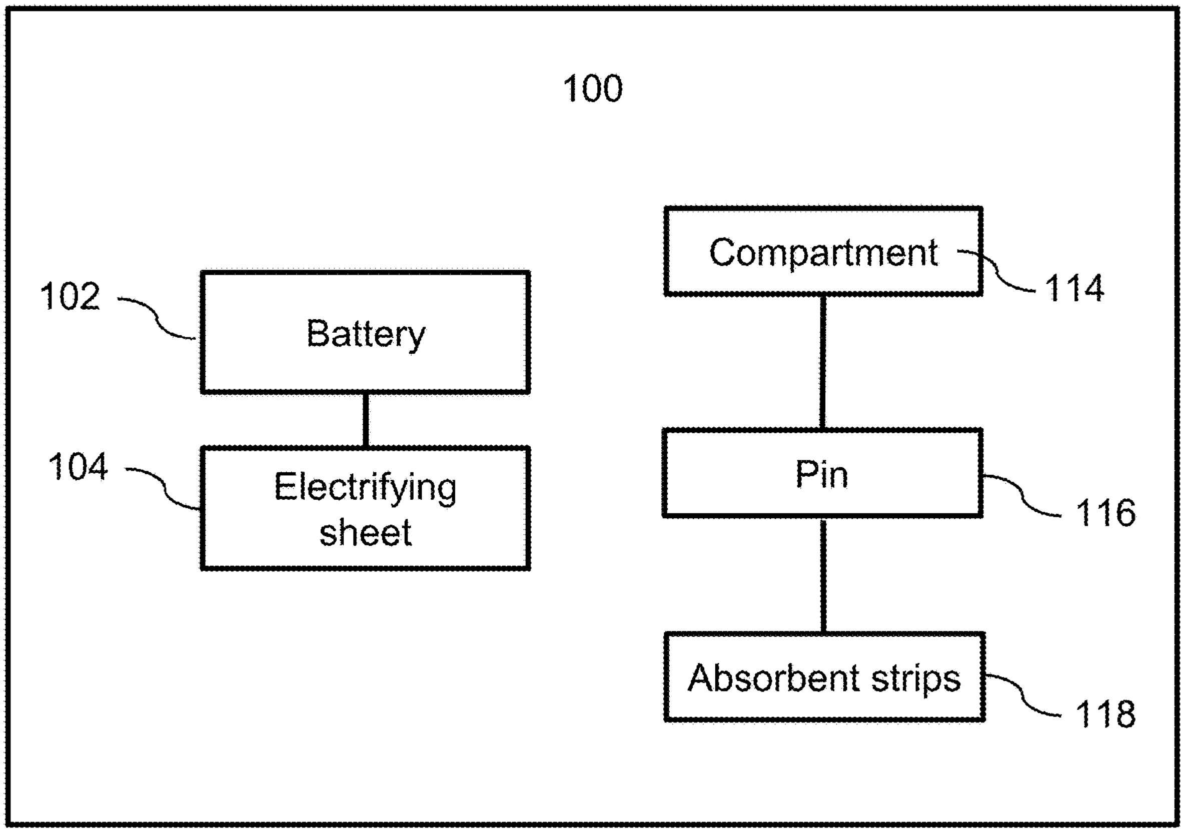

FIG. 6: A block diagram of a lice killer device, in accordance with some embodiments.

Figure 7:
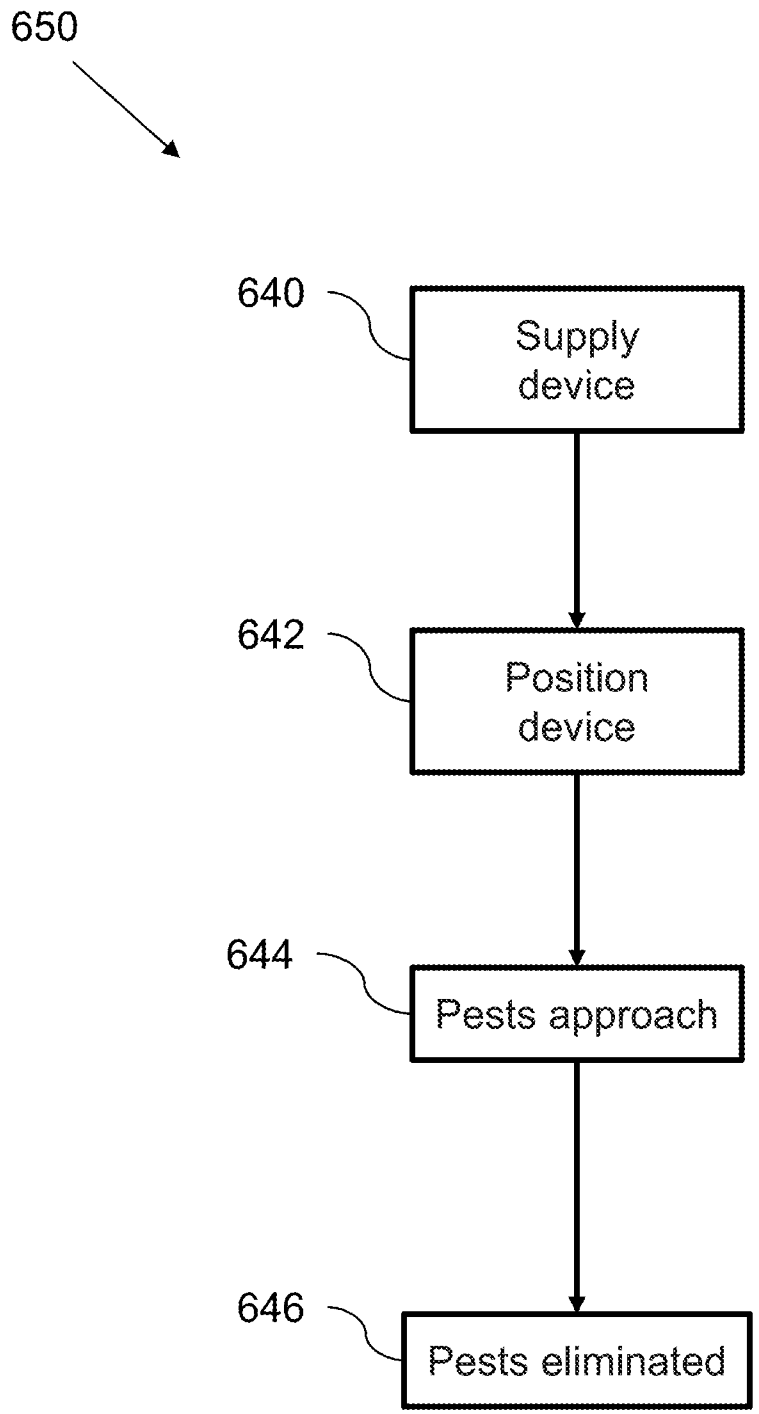

FIG. 7: A flow chart illustration of a method of passively eliminating pests from a subject using a lice killer device, in accordance with an embodiment of the current invention.

Figure 8:
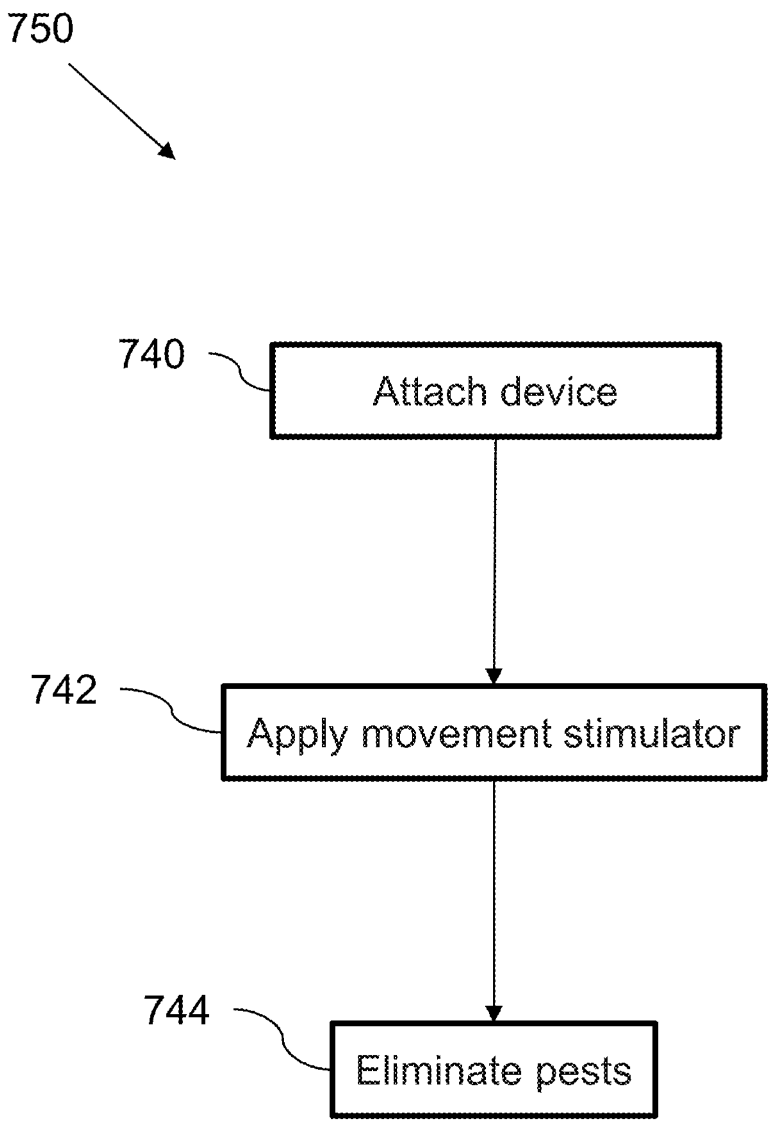

FIG. 8: A flow chart of a device for passively eliminating pests from a subject using a lice killer device, in accordance with an embodiment of the current invention.

Figure 9:
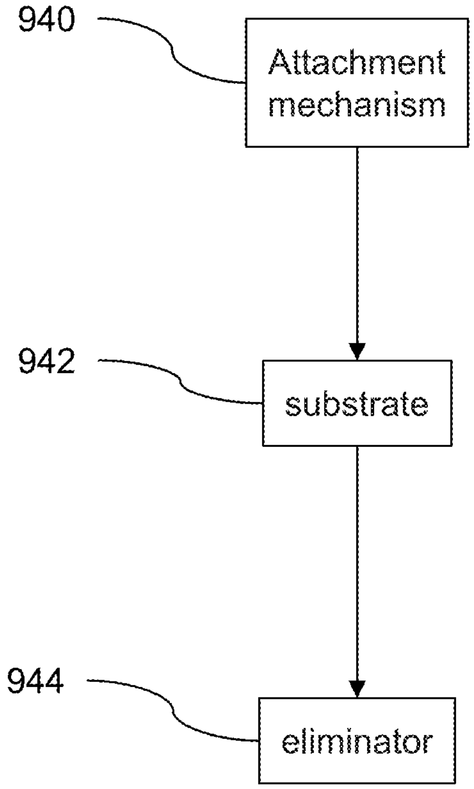

FIG. 9 is a block diagram of a device for passively eliminating pests from a subject in accordance with an embodiment of the current invention.

DESCRIPTION OF SPECIFIC EMBODIMENTS OF THE INVENTION

The present invention, in some embodiments thereof, relates to a system and method for treating head lice, and, more particularly, but not exclusively, to a system to trap and/or eradicate head lice from a subject passively.

Overview

The invention will be understood from the following detailed description of embodiments of the invention, which are meant to be descriptive and not limiting. For the sake of brevity, some well-known features are not described in detail.

Some embodiments relate to a system and method for treating head lice. According to some embodiments, the system and method may be configured to trap and/or eradicate head lice from a subject passively. According to some embodiments, the system may include a wearable device. According to some embodiments, the wearable device may be an electrical device, electric-chemical device, chemical device, a physical device, or any combination thereof.

In some embodiments, a system and/or method of the current invention may be used to eliminate other pest and/or may used on non-human hosts. For example, a device may be used to eliminate ticks, flees and/or mites. In some embodiments, the invention may be used on pets, helper animals (e.g., seeing eye dogs, police dogs) and/or therapeutic animals for example to eliminate fleas on a dog and/or cat and/or rodent (e.g., rabbit, Guinea pig) and/or mites of a bird (e.g., parrot, canary). Some embodiments of the invention may be used on livestock (e.g., dairy cows, poultry).

In some embodiments, a pest eliminator may neutralize a pest. For example, the pest may be killed and/or trapped and/or poisoned and/or demobilized and/or sterilized.

According to some embodiments, the lice killer device may be included in an item of clothing worn on the head of the subject (such as, a hat, cap, helmet, headband, bandana, toy, etc.). Optionally, the device may be attached to bedding, e.g., pillow case, clothing, etc. an object for use by an animal. Optionally, the device may be worn under clothing and/or placed near the body and/or may contact the body of the subject. Optionally, the device may be shielded from contact with the body, from contact with other people and/or animals, such as pets. Optionally, the device may include an attachment means, e.g., one or more straps, adhesive, etc. Optionally, the device may be fitted to the body, built into an item of clothing and/or attached to an item of clothing.

According to some embodiments, the lice killer device may include one or more electrifying sheets. Optionally, the electrifying sheet may be configured to kill the head lice passively. Optionally, the electrifying sheet may include a current passing through it, which may kill the head lice when they contact electrodes of opposite polarity of the electrifying sheet, e.g., as they climb on and/or over the sheet.

According to some embodiments, the one or more electrifying sheets may be connected at a focal point. Optionally, the voltage source for the electrifying sheets may be at the focal point. Optionally, the voltage source may be a battery. Optionally, the focal point may include a battery. Optionally, the battery may be rechargeable.

According to some embodiments, the width of an electrifying sheet may vary along their length. For example, the width of the electrifying sheet may increase as it extends away from the focal point. Optionally, the width of the electrifying sheet may increase along its length by a factor of about 0.5, and/or about 0.75, and/or about 1, and/or about 1.5, and/or about 2, and/or about 2.5 and/or about 3.

According to some embodiments, an electrifying sheet may be flexible. Optionally, the electrifying sheet may be configured to fit a subject's head. Optionally, an electrifying sheet may be adjusted to fit a subject's head.

According to some embodiments, an electrifying sheet may comprise a mesh and/or a grill and/or intercalating protrusions and/or printed circuit board (PCB). Optionally, the mesh and/or a grill and/or intercalating protrusions and/or printed circuit board may be electrically conducting. Optionally, the mesh and/or a grill and/or intercalating protrusions and/or printed circuit board may be connected to a voltage source. Optionally, the distance between the electrodes may be sufficient to kill head lice. Optionally, the distance between protrusions, mesh wires, grill, PCB, etc. may be sufficient to kill head lice on contacting electrodes of opposite polarity. Optionally, electrodes of opposite polarity may be configured to be sufficiently distant to kill head lice when the head lice contact both electrodes, e.g., by climbing on the electrifying sheet. Optionally, the electrodes may be recessed. Optionally, the device may be positioned such that the head lice may contact the device through their own movement, e.g., the device may be turned on and the head lice may climb on to the device, contacting electrodes of opposite polarity, thereby killing them.

According to some embodiments, the voltage source may provide a voltage ranging between about 1.5 volts to about 3.5 volts. Optionally, the voltage source may be configured to kill lice and/or nits by disrupting their nervous systems. Optionally, the high voltage may cause a brief electrical shock that disrupts the lice's nervous system, thereby killing them quickly and humanely. Optionally, the voltage source may be configured to electrocute the lice and/or nits.

According to some embodiments, the voltage source may provide a very low current, e.g., in the microampere range. Optionally, the current may be very low to prevent a subject from being electrocuted on contact with electrodes of opposite polarity of the one or more electrifying sheets.

According to some embodiments, the device may include shielding for the electrifying sheet, e.g., made of rubber, elastomer, plastic, polyester, nylon or any combination thereof. Alternatively or additional, the shielding may include foil, braid, such as a thin layer of aluminum, copper, steel. For example, the shielding may include an insulated materials and/or may be insulated from and/or separated from the electrodes. Optionally, the device may include an insulating sheet. Optionally, the insulating sheet may be non-conducting. Optionally, the insulating sheet may be configured to protect the subject's head. Optionally, one or more electrifying sheets may be built into an item worn on the head of the subject, e.g., a hat, cap, helmet, headband, bandana, toy, etc. Additionally or alternative a pest eliminator may be in the form of a pendant, a bracelet, a necklace, bedclothes (e.g., a pillow case, a sheet).

In some embodiments, a pest eliminator (e.g., electrodes and/or adhesive) may be shielded. For example, electrodes may be shielded by a non-conducing protrusion. Optionally, the protrusion may distance electrodes on a sheet from large surfaces (e.g., skin) while allowing smaller objects (e.g., a louse and/or a body part of a louse) to contact the electrodes. For example, shielding may include a grill and/or electrodes may be recessed into a substrate (e.g., recessed into a plastic sheet). Alternatively or additionally, electrodes Additionally or alternatively, electrodes may be positioned inside a trap (e.g., a compartment into which pests wander and/or into which the pest is lured).

In some embodiments, electrodes may be used to eliminate a pest. Optionally, as an alternative to electrodes, a pest may be eliminated by chemicals (e.g., poison) and/or an adhesive (e.g., the pest may be adhered to an inner portion of a trap) and/or radiation (e.g., UV light). Alternatively or additionally, a pest may be treated and released (for example, treatment may include sterilizing a pest and releasing it to prevent others from breeding).

According to some embodiments, the device may include a means of stimulating movement of the head lice. Optionally, the movement stimulator may be a pheromone, an amino acid, an herb, an herbal extract, a chemical, a physical stimulation, e.g., a light source, a vibration source, or any combination thereof. Optionally, the stimulator may be chemical, e.g., to attract and/or repulse head lice. Non-limiting examples of movement stimulators include pheromones, Soursop (*Annona muricata* L.), coconut, tea tree oil, lavender oil, *Eucalyptus* oil, rosemary oil, lemon grass oil, vinegar, neem, garlic, masha, peppermint oil and/or any combination thereof. Optionally, the movement stimulators may encourage the head lice to move on and/or over the electrifying sheet.

According to some embodiments, a movement stimulator may be built into the device. According to some embodiments, the movement stimulator may be supplied separately. According to some embodiments, the movement stimulator may be applied separately, e.g., as a lotion, shampoo, oil, etc.

According to some embodiments, the device may be configured to include a means of distributing the movement stimulator. Optionally, the movement stimulator may be absorbed onto one or more fluid absorbent sheets and/or straps and/or strips and/or wicks, etc. Optionally, the absorbent strips may wick the movement stimulator from a compartment containing a movement stimulating fluid. Optionally, the movement stimulator may be included in a replaceable capsule.

According to some embodiments, the compartment may be located at the focal point. Optionally, the compartment may include a cap. Optionally, the compartment may include a pin. Optionally, the pin may extend from the floor of the compartment. Optionally, the pin may be configured to pierce the base of the capsule. Optionally, the pin may be configured to pierce the base of the capsule on capping of the compartment. Optionally, the compartment may include one or more holes for egress of the capsule fluid. Optionally, the compartment may be connected to the one or more absorbent strips. Optionally, the one or more absorbent strips may absorb fluid from the capsule. Optionally, the fluid absorbed by the one or more absorbent strips may attract and/or repulse the head lice.

According to some embodiments, the capsule may include one or more lice killing substances, e.g., a poison such as permethrin, ivermectin, piperonyl butoxide, pyrethrin, malathion, or any combination thereof.

According to some embodiments, the absorbent strips may be replaceable. Optionally, the absorbent strips may comprise an absorbent fabric, paper, wool cotton, etc. Optionally, the absorbent strips may extend from the compartment for transporting, e.g., by diffusion, of the movement stimulator.

According to some embodiments, the device may include an additional passive means of eliminating head lice. Optionally, the additional passive means of eliminating head lice may include a lice trap, poison, poisonous adhesive, adhesive, etc. Optionally, the movement stimulator may be configured to attract the head lice to a lice eliminator, e.g., an electrifying sheet, trap, poison, poisonous adhesive, adhesive, or any combination thereof. Optionally, the head lice may be eliminated by trapping, electrocuting, poisoning, adhering them to a surface, etc.

According to some embodiments, the lice killing device may be supplied and positioned on the head of a subject. Optionally, the electrifying sheet may be electrified. Optionally, a movement stimulator may be applied. Optionally, the lice may contact the device through their own movement, thereby eliminating the lice.

EXEMPLARY EMBODIMENTS

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The reference numbers have been used to point out elements in the embodiments described and illustrated herein, in order to facilitate the understanding of the invention. They are meant to be merely illustrative, and not limiting. Also, the foregoing embodiments of the invention have been described and illustrated in conjunction with systems and methods thereof, which are meant to be merely illustrative, and not limiting.

Reference is now made to the figures.

FIG. 1 is a schematic illustration of a lice killer device in a deployed state, in accordance with some embodiments. For example, device 10 may include a focal point 14 including a battery 78 including a positive electrode 16A and a negative electrode 16B; and one or more electrifying sheets 12 extending from focal point 14. Optionally, the focal point includes connectors to be connected to the electrifying sheets 12. Alternatively or additionally, the focal point may be permanently attached to the sheets 12. For example, a focal point may include between 1 to 6 sheets and/or connectors, between 6 to 12 sheets and/or connectors and/or between 12 to 24 sheets and/or connectors and/or more. Optionally, each of the sheets may be connected to a separate connector. Alternatively or additionally, multiple sheets may be connected to a single connector. Optionally, an indicator may indicate may a pest has been eliminated. For example, a LED may light for a short time (e.g., between 1 and 5 seconds and/or between 1 to 3 seconds and/or between 0.1 to 2 seconds) to indicate that a bug has been electrocuted. Optionally, there may be multiple indicators. For example, there may be an indicator by each connection indicating when a pest has been electrocuted on a sheet connected to that connection. In some embodiments, the system may communicate a total number of pests eliminated in a session and/or over a time period. For example, the system may include a display that shows how many lice killed in one sitting and/or the data may be sent to a personal computing device of the user (e.g., a smartphone and/or a personal computer). In some embodiments, the system may include a noise maker (e.g., a loud speaker that plays a sound [e.g., a sparking sound and/or a sizzling sound and/or a message) when a pest is eliminated.

In some embodiments, the system my include fail protection. For example, if one sheet malfunctions, other sheets may be kept running. For example, if one of the sheet has a long term and/or high current (e.g., if the time of the short is longer than a threshold time (e.g., longer than electrocuting a louse) and/or the current is higher than a threshold current (e.g., the current to electrocute a louse)) than the sheet will be isolated and/or other sheets will continue to function.

According to some embodiments, the width of the electrifying sheets may vary along their length. Optionally, the width of the electrifying sheets may increase as it extends away from the focal point. Optionally, the width of the electrifying sheet may increase along their length by a factor of about 0.5, and/or about 0.75, and/or about 1, and/or about 1.5, and/or about 2, and/or about 2.5 and/or about 3.

FIG. 2 is an enlarged section 56 of an end of one of the extension portions of the lice killer device of FIG. 1, in accordance with some embodiments. For example, each electrifying sheet 12 may include a mesh 54, grill, PCB, intercalating protrusions, etc. Optionally, the electrifying sheet 12 may be electrified, e.g., by attachment to electrode 16A and 16B. Optionally, the distance between mesh 54, grill, PCB, intercalating protrusions, may be configured to be near one another, such that a louse 20 contacting two electrodes of opposite polarity and are electrified to an extent of being killed.

According to some embodiments, the distance between the electrodes may be smaller than the length of the average louse. Optionally, the distance between the electrodes may range between about 1 mm to about 5 mm, and/or between about 1.5 mm to about 4 mm, and/or between about 2 mm to about 3 mm.

FIG. 3 is a schematic illustration of a lice killer device positioned on a subject's head, in accordance with some embodiments. For example, electrifying sheets 12 may be adjusted and/or folded in relation to focal point 14 to fit a subject, e.g., the electrifying sheets may be built into an item of clothing (such as a hat 52), surrounded by a strap 22, etc.

According to some embodiments, device 10 may further include a movement stimulator. Optionally, the movement stimulator may be a substance 64, preferably a fluid for stimulating movement of the lice, e.g., to increasing the possibility of the lice contacting electrodes 16A and 16B of opposite polarity. Optionally, the movement stimulator may attract or repel the lice. Optionally, the movement stimulator may be supplied in a replaceable capsule 32.

According to some embodiments, device 10 may a compartment 36 for containing substance 64. Optionally, compartment 36 may include a cap 38 and may be connected to a plurality of absorbent strips 26, extending from a plurality of compartment openings 46 in compartment 36, for transporting, by diffusion, substance 64. Optionally, the movement stimulator may encourage the lice to move onto electrifying sheets 12 where they may be eradicated.

FIG. 4 is a schematic illustration of a front sectional view of a lice killer device, in accordance with some embodiments. For example, capsule 32 may include a rigid ceiling 70A and a bag 70B extending from rigid ceiling 70A.

According to some embodiments, compartment 36 may include pin 30 extending from the floor of compartment 36. Optionally, sealing compartment 36 with a cap 38 (capping) may press the base of capsule 32 onto pin 30, puncturing bag 70B and releasing the movement stimulator.

According to some embodiments, capping may be applied by adjustably rotating cap 38 on its thread 72A in relation to a thread 72B of compartment 36. Alternatively or additionally, the cap 38 may be connected to the compartment 36 by another means, for example, an interference element, and/or a friction element and/or a clip and/or an elastic fastener etc. Optionally, the more pressure applied by the extent of the rotation, the larger perforation of bag 70B, and therefore, the greater the amount of substance 64 released from bag 70B to compartment 36.

Each absorbent strip 26 may be housed within pipe 42. Optionally, pipe 42 may extend the length of absorbent strip 26. Optionally, pipe 42 may including a plurality of openings for distribution of substance 64 therethrough. Optionally, pipe 42 may not extend the length of absorbent strip 26. Optionally, substance 64 may be wicked by the absorbent strip and distributed by diffusion.

According to some embodiments, electrifying sheet 12 may include a non-conducting protrusion, for example, shielding 53 therebelow. Optionally, shielding 53 may protect the head of the subject from contact with electrodes 16*a*, 16*b* (e.g., to prevent a person from getting a painful shock where he has a bald spot).

FIG. 5 is a schematic illustration of a longitudinal cross section of electrifying sheet of a lice killer device, in accordance with some embodiments. For example, device 10 may include a flexible insulating sheet 12, shielding 54, one or more electrodes 16*a*, 16*b* including a plurality of positive electrodes 16*a* and negative electrodes 16*b*. Optionally, electrodes 16*a*, 16*b* may be shielded from skin. For example, a sheet may have strips of shielding 54 that protrude from the sheet further than the electrodes 16*a*, 16*b*. For example, when the sheet 12 is brought close to a large relatively flat surface (e.g., with a radius of curvature greater than a centimeter) the strips prevent the electrodes 16*a*, 16*b* from contacting the skin. On the other hand, a small object such as a louse easily fits in the space between the strips and contacts and shorts circuits the positive electrode 16*a* to the negative electrode 16*b* causing electrocution, stunning etc.

FIG. 6 is a block diagram of a lice killer device, in accordance with some embodiments. For example, device 100 is supplied 640 for eliminating lice. Optionally, device 100 includes a battery 102 and one or more electrifying sheets 104 configured to be electrified to kill lice. Optionally, device 100 may include compartment 114 for a capsule (not shown) containing a movement stimulator, a pin 116 configured for puncturing the capsule, and a plurality of absorbent strips 118 configured for distribution of the movement stimulator.

FIG. 7 is a flow chart illustration of a method of passively eliminating pests from a subject using a lice killer device, in accordance with an embodiment of the current invention. For example, in method 650, a lice killing device is supplied. The device may be an electrical device, electric-chemical device, chemical device, a physical device, or any combination thereof. The device may be positioned 642 on or in the vicinity of the subject. Optionally, the device may be included in an item worn on the head of the subject (such as, a hat, cap, helmet, headband, bandana, toy, etc.). Optionally, the device may be attached to bedding, e.g., pillow case, clothing, etc. Optionally, the device may be worn under clothing and/or placed near the body and/or may contact the body of the subject. Optionally, the device may be shielded from contact with the body, from contact with other people and/or animals, such as pets. Optionally, the device may include an attachment means, e.g., one or more straps, adhesive, etc. Optionally, the device may be fitted to the body, built into an item of clothing and/or attached to an item of clothing.

Pests (such as head lice) may approach the device 644. Pests contact the electrified electrifying sheet, contacting electrodes of opposite polarity thereby eliminating the pests 646, passively.

According to some embodiments, the device may include an additional passive means of eliminating head lice. Optionally, the additional passive means of eliminating head lice may include a lice trap, poison, poisonous adhesive, adhesive, etc. Optionally, the movement stimulator may be configured to attract the head lice to a lice eliminator, e.g., electrifying sheets, trap, poison, poisonous adhesive, adhesive, or any combination thereof. Optionally, the head lice may be eliminated by trapping, electrocuting, poisoning, adhering them to a surface, etc.

According to some embodiments, the lice killing device may be supplied and positioned on the head of a subject. Optionally, the electrifying sheets may be electrified. Optionally, a movement stimulator may be applied. Optionally, the lice may contact the device through their own movement, thereby eliminating the lice.

FIG. 8: A flow chart of a device for passively eliminating pests from a subject using a lice killer device, in accordance with an embodiment of the current invention. For example, in method 750, the device is attached 740 by an attachment mechanism to a subject and/or in the vicinity of a subject. Optionally, the device may apply 742 a means of stimulating movement of the head lice. Optionally, the movement stimulator may be a pheromone, an amino acid, an herb, an herbal extract, a chemical, a physical stimulation, e.g., a light source, a vibration source, or any combination thereof. Optionally, the stimulator may be chemical, e.g., to attract and/or repulse head lice. Non-limiting examples of movement stimulators include Soursop (*Annona muricata* L.), coconut, tea tree oil, lavender oil, *Eucalyptus* oil, rosemary oil, lemon grass oil, vinegar, neem, garlic, masha, and/or peppermint oil. Optionally, the movement stimulators may encourage the head lice to move on and/or over a plurality of the electrified electrifying sheets, contacting electrodes of opposite polarity and thereby eliminating the pests 744, passively.

According to some embodiments, the lice killing device may be supplied and positioned on the head of a subject. Optionally, the electrifying sheets may be electrified. Optionally, a movement stimulator may be applied. Optionally, the lice may contact the device through their own movement, thereby eliminating the lice.

FIG. 9 is a block diagram of a device for passively eliminating pests from a subject in accordance with an embodiment of the current invention.

In some embodiments, a pest eliminating system includes an attachment mechanism 940 to attach it to a host. For, example, the attachment mechanism 940 may include a hat and/or a headscarf for attaching the system to a head of a person and/or a dog sweater for placement on a pet and/or a pendant for placement on a necklace and/or bracelet and/or a pillow case etc.

In some embodiment, a pest eliminating system may include a substrate 942 holding a pest eliminator 944. For example, the substrate and/or eliminator 944 may be held close to a place on the host where pests are present. For example, the system may be held near hair, and/or near folds in skin and/or body opening (e.g., ears or nose). In some cases, the substrate 942 may insulator an insulator and/or semiconductor and/or the eliminator may include an electrode and/or a power source and/or a transformer (e.g., a capacitor, a rectifier) to channel an effective electrical charge to eliminate a pest. For example, electrodes may be deposited and/or etched onto a flexible sheet. Alternatively or additionally, the eliminator may include other means to eliminate the pest, for example, chemicals and/or traps and/or attracting bait and/or adhesives. In some embodiments, the substrate 942 and/or the eliminator 844 may include shielding.

In the figures and description herein, the following reference numbers (Reference Signs List) have been mentioned:

10: the lice killer device;
12: electrifying sheet;
14: focal point;
16A and 16B: positive and negative electrodes;
20: louse;
22: strap;
24: subject;
26: absorbent strap;
30: pin;
32: capsule;
36: compartment;

38: cap;
42: pipe;
46: compartment openings;
50: pipe opening;
53: shielding;
54: mesh of electrodes;
56: enlarged view zone;
64: movement stimulator;
70A: rigid surface of capsule 32;
70B: bag of capsule 32;
72A, 72B: complementary threads;
78: battery;
80: rotating cap 38;

GENERAL

The foregoing description and illustrations of the embodiments of the invention have been presented for the purpose of illustration, and are not intended to be exhaustive or to limit the invention to the above description in any form.

It is expected that during the life of a patent maturing from this application many relevant building technologies, artificial intelligence methodologies, computer user interfaces, image capture devices will be developed and the scope of the terms for design elements, analysis routines, user devices is intended to include all such new technologies a priori.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described herein. In case of conflict, the patent specification, including definitions, will control. In addition, the materials, methods, and examples are illustrative only and are not intended to be necessarily limiting.

Any term that has been defined above and used in the claims, should be interpreted according to this definition.

The reference numbers in the claims are not a part of the claims, but rather used for facilitating the reading thereof. These reference numbers should not be interpreted as limiting the claims in any form.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween. When multiple ranges are listed for a single variable, a combination of the ranges is included (for example the ranges from 1 to 2 and/or from 2 to 4 includes the combined range from 1 to 4).

It is appreciated that certain features of the invention, which are, for clarity, described in the context of separate embodiments, may be provided in combination in a single embodiment. Conversely, various features of the invention, which are, for brevity, described in the context of a single embodiment, may be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for eliminating lice on a host, comprising:

a passive wearable device configured to be worn on a host infected with lice, including:

an eliminator including opposite charged electrodes distanced apart less than a length of an average louse to neutralize the lice;

an attachment mechanism for holding the eliminator in a position where movement of the lice will bring the lice to be neutralized by the eliminator, and protruding non-conductive shielding, wherein the electrodes are recessed relative to the protruding non-conductive shielding and the protruding non-conductive shielding extending beyond the electrodes: the protruding non-conductive shielding configured to inhibit contact between the electrodes and skin of the host while permitting the lice to contact electrodes of opposite polarity via said movement of the lice.

2. The system of claim 1, wherein the eliminator includes one or more electrifying sheets.

3. The system of claim 2, wherein the one or more electrifying sheets connect at one or more focal points.

4. The system of claim 1, further comprising a stimulator configured to stimulate movement of the lice.

5. The system of claim 4, wherein the stimulator is configured to repel the lice.

6. The system of claim 4, wherein the stimulator is configured to attract the lice.

7. The system of claim 3, further comprising a compartment located at at least one of said one or more focal points of the device and configured for storing a stimulator configured to stimulate the movement of the lice.

8. The system of claim 7, wherein the compartment comprises a plurality of members extending through openings in the compartment for distributing the stimulator, the members including at least one of fluid absorbent sheets, straps, strips and wicks.

9. The system of claim 4, wherein the stimulator is selected from the group consisting of light, vibration, pheromones, Soursop, coconut, tea tree oil, lavender oil, *Eucalyptus* oil, rosemary oil, lemon grass oil, vinegar, neem, garlic, masha, peppermint oil, and any combination thereof.

10. The system of claim 1, wherein the stimulator comprises a light source and a vibration source configured to encourage natural locomotion of the lice from the host towards a neutralization area of the eliminator.

11. The system of claim 1, wherein the protruding non-conductive shielding includes strips of shielding.

12. A method for passively eliminating lice, the method comprising:

positioning a passive wearable lice eliminator on a host infected with lice using an attachment mechanism;

contacting by the lice through movement of the lice with electrodes of opposite polarity of the eliminator wherein spacing between the electrodes is smaller than an average length of a louse;

neutralizing the lice as a result of said contacting; and inhibiting contact between the electrodes and skin of the host while permitting the lice to contact the electrodes by recessing the electrodes relative to protruding non-conductive shielding.

13. The method of claim 12, further comprising stimulating said movement of the lice.

14. The method of claim 13, wherein the stimulating includes supplying one item selected from the group consisting of light, vibration, pheromones, Soursop, coconut, tea tree oil, lavender oil, *Eucalyptus* oil, rosemary oil, lemon grass oil, vinegar, neem, garlic, masha, peppermint oil, and any combination thereof.

15. The method of claim 13, wherein the stimulating is by a chemical repellent.

16. The method of claim 13, wherein the stimulating is by supplying a light source and a vibration source configured to encourage natural locomotion of the lice towards a neutralization area of the eliminator.

17. The method of claim 14, wherein the stimulating includes attracting the lice.

18. The method of claim 13, wherein said stimulating includes distributing a stimulator from a focal-point compartment on the passive wearable lice eliminator through at least one opening via at least one extending member.

* * * * *